United States Patent [19]

Leroy

[11] 4,034,747
[45] July 12, 1977

[54] CERVICAL COLLAR

[75] Inventor: Pierre L. Leroy, Wilmington, Del.

[73] Assignee: New Research and Development Lab., Inc., Wilmington, Del.

[21] Appl. No.: 673,152

[22] Filed: Apr. 2, 1976

[51] Int. Cl.² .................................... A61F 5/00
[52] U.S. Cl. .................... 128/68.1; 128/DIG. 23
[58] Field of Search ......... 128/68.1, DIG. 23, 87 B, 128/388, 387

[56] References Cited

U.S. PATENT DOCUMENTS

| 448,128 | 3/1891 | Crisp et al. | 128/388 |
|---|---|---|---|
| 2,818,063 | 12/1957 | Smith et al. | 128/DIG. 23 |

OTHER PUBLICATIONS

Down Bros. Catalog May 18, 1966 p. G-122.
Orthopaedics Appliances Atlas 1952 pp. 93-95.

*Primary Examiner*—Lawrence W. Trapp
*Attorney, Agent, or Firm*—Connolly and Hutz

[57] ABSTRACT

A cervical collar applies body heat to the area of treatment and minimizes pressure upon the brachial plexus. The collar extends lengthwise from the occiput to the dorsal-four so as to be occipito-sinous and has a bi-acromial width which likewise extends through the dorsal-four.

22 Claims, 11 Drawing Figures

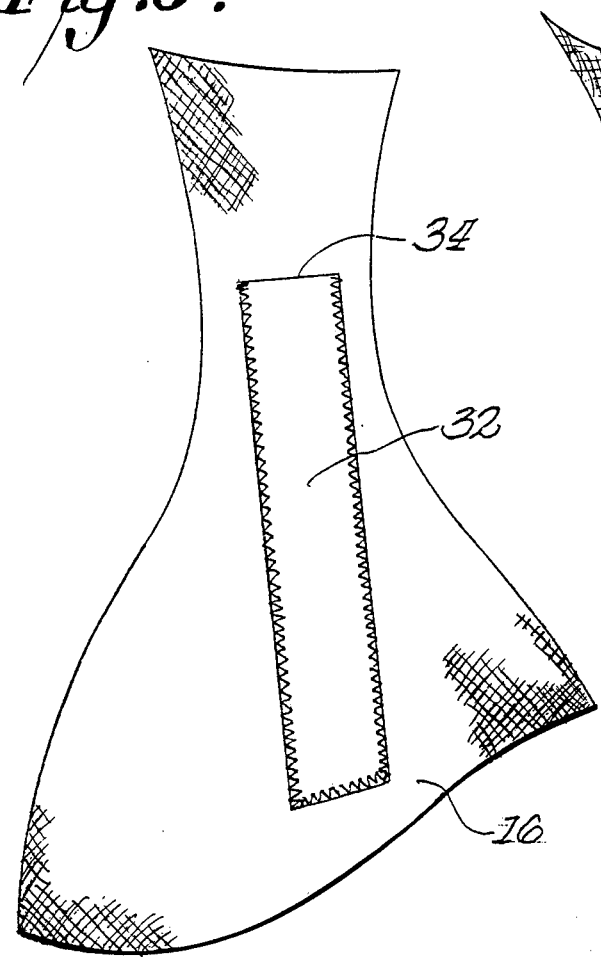
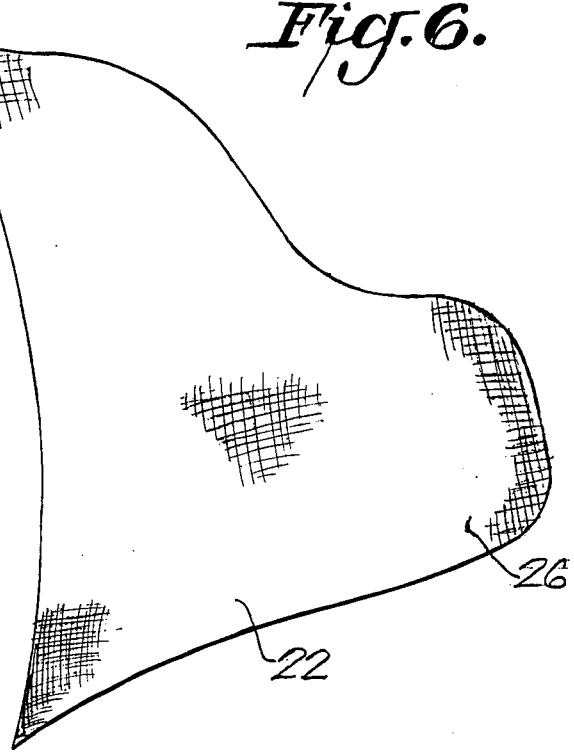
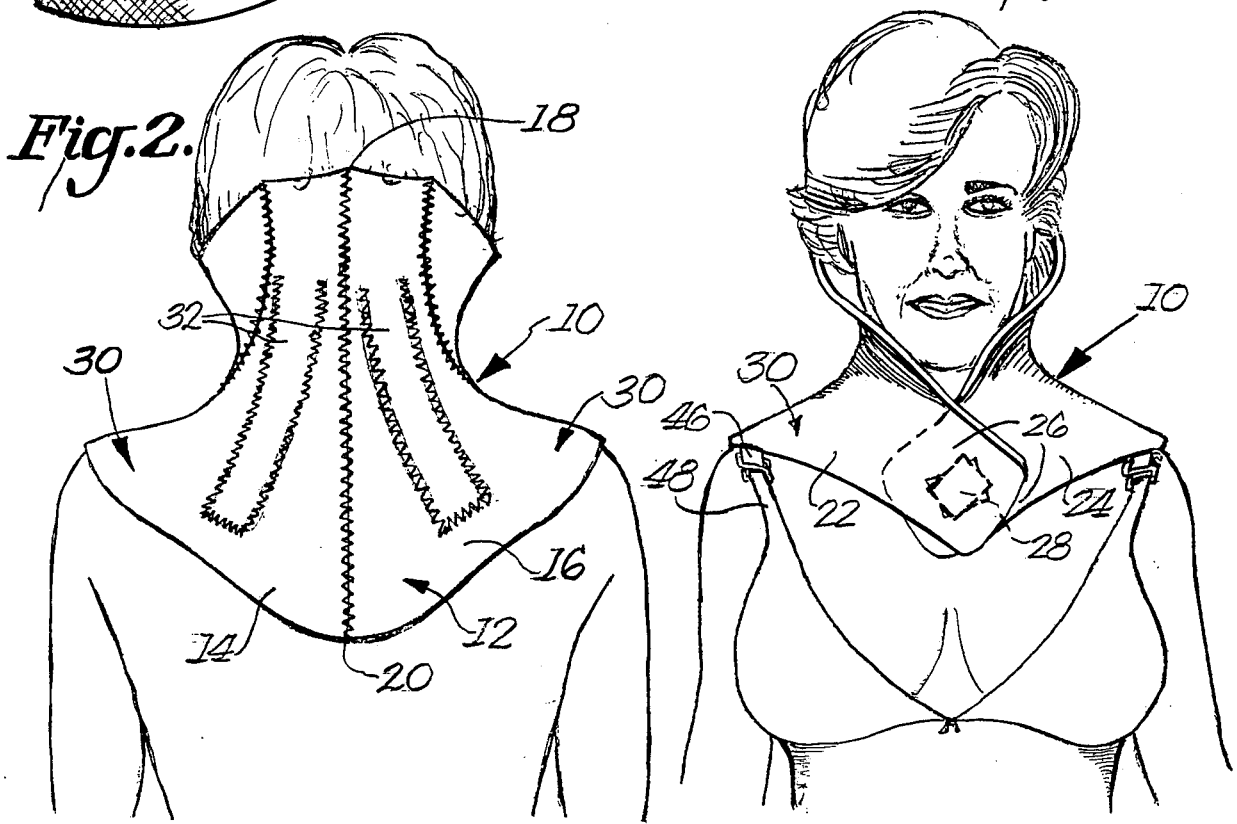

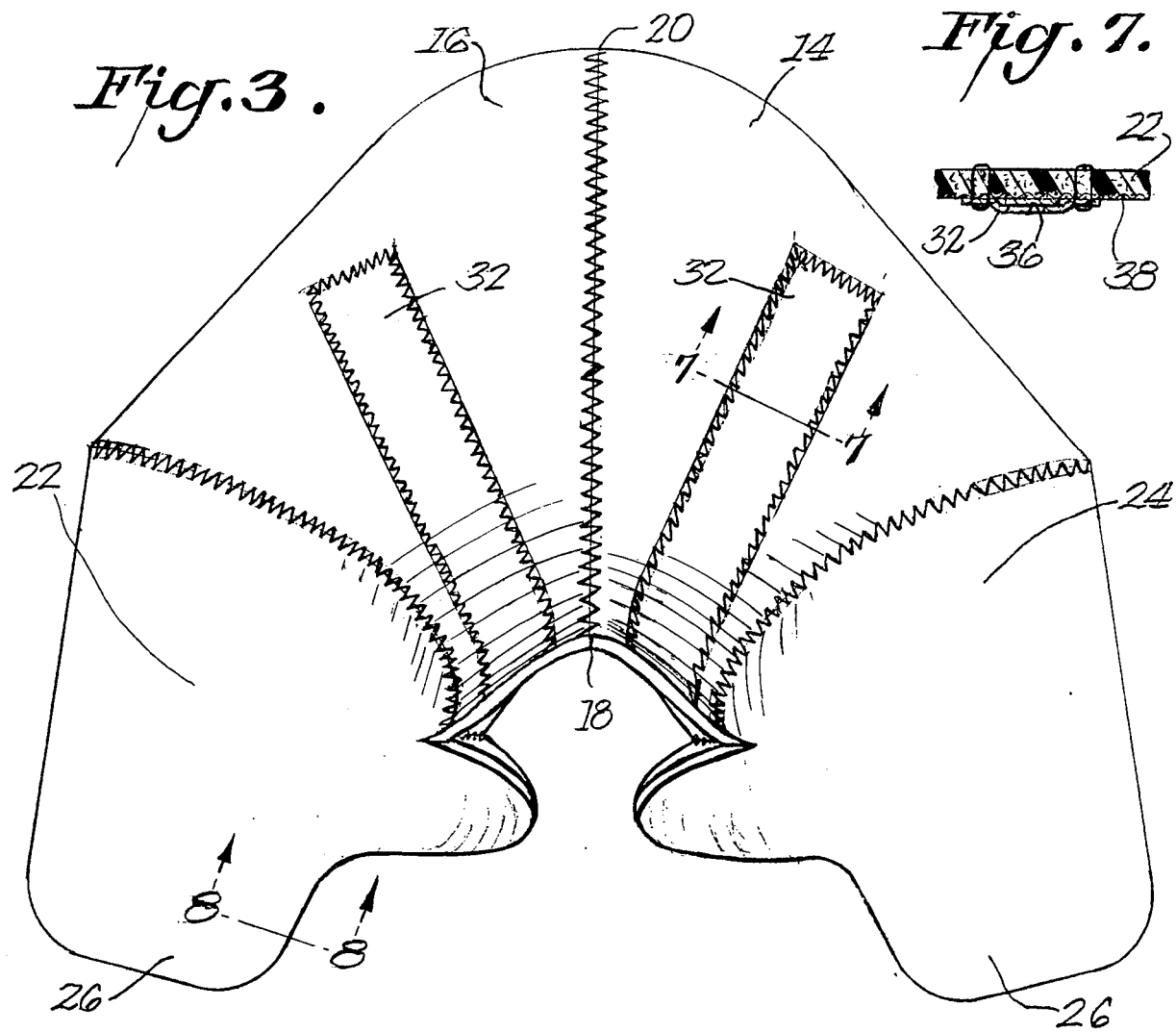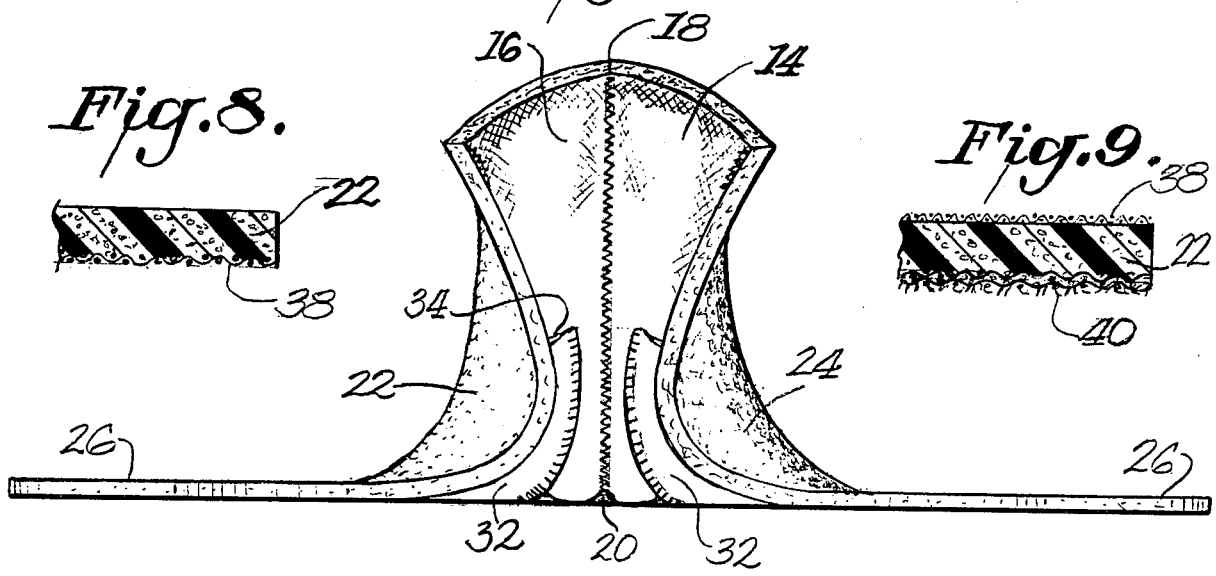

ial application thereto as, for example, applied by electrodes.
CERVICAL COLLAR

BACKGROUND OF THE INVENTION

Various cervical collars have long been known and used by the prior art. A major disadvantage with conventional cervical collars is that such collars cause undesirable pressure on the brachial plexus. This problem is praticularly acute with female patients and more particularly with such patients as are heavy breasted since the weight of the breasts also cause undesirable pressure. Ideally, pressure should be spread away from the brachial plexus whether such pressure is being applied by use of the collar itself or from the weight of the user's breasts. Ideally, recuperation is enhanced where heat is also applied to the treated area. Still further, pain could be alleviated by electrical application thereto as, for example, applied by electrodes.

SUMMARY OF THE INVENTION

An object of this invention is to provide a cervical collar which advantageously avoids undesirable pressure on the brachial plexus.

A further object of this invention is to provide such a cervical collar which is so constructed so as to automatically apply heat to the treated area.

A still further object of this invention is to provide such a cervial collar which is particularly adapted for use by women.

A yet further object of this invention is to provide an arrangement for conveniently disposing electrodes in contact with the skin in the sensitive area.

In accordance with this invention a cervical collar is formed with a central section which extends from the user's occiput to the dorsal-four (D-4) and which has wing sections which rest upon the shoulders of the user, namely, from one acromia to the other.

In a preferred embodiment of this invention the collar is made from a heat insulating, flexible and conformable material which is capable of closely contacting and conforming to the anatomy of the user and which extends over a sufficiently large area to retain the body heat and thereby meaintains it in the area being treated.

In accordance with a further aspect of this invention the cervical collar is so designed as to be compatible with the user's bra. In this respect the collar may contain clips or other suitable means of attachment in the general area of the acromia to which the straps of the bra would be secured for providing the necessary support at areas away from the brachial plexus. Alternatively, a conventional bra may be used by disposing the straps over the collar in the acromial areas and by using a sufficiently soft material for the collar so that the straps sink somewhat into the collar to be retained in that area.

A significant feature of this invention is that the collar may be used as a convenient means for applying electrodes against the skin of the user. In this respect such electrodes would be suitably fastened to the inner surface of the collar and in contact with the skin.

In accordance with a still further aspect of this invention the collar may be so shaped as to accommodate the ear lobes of the user so that a user may wear earrings without interference from the collar and so as to barely graze or take purchase just beneath the jaw thereby permitting relative jaw movement to facilitate speaking or swallowing.

THE DRAWINGS

FIG. 1 is a front elevation view showing a cervical collar in accordance with this invention;

FIG. 2 is a rear elevation view of the collar in FIG. 1;

FIG. 3 is a top plan view to scale showing the collar of FIGS. 1-2 in a generally flattened condition;

FIG. 4 is a front elevation view to scale of the collar of FIG. 3;

FIG. 5 is a plan view to scale of one of the panels in the central section of the collar of FIGS. 3-4;

FIG. 6 is a plan view to scale of a further panel of the collar of FIGS. 3-4;

FIG. 7 is a cross-sectional view taken through FIG. 3 along the line 7—7;

FIG. 8 is a cross-sectional view taken through FIG. 3 along the line 8—8;

FIG. 9 is a cross-sectional view similar to FIG. 8 showing a modified form of this invention;

DETAILED DESCRIPTION

Figure 10:
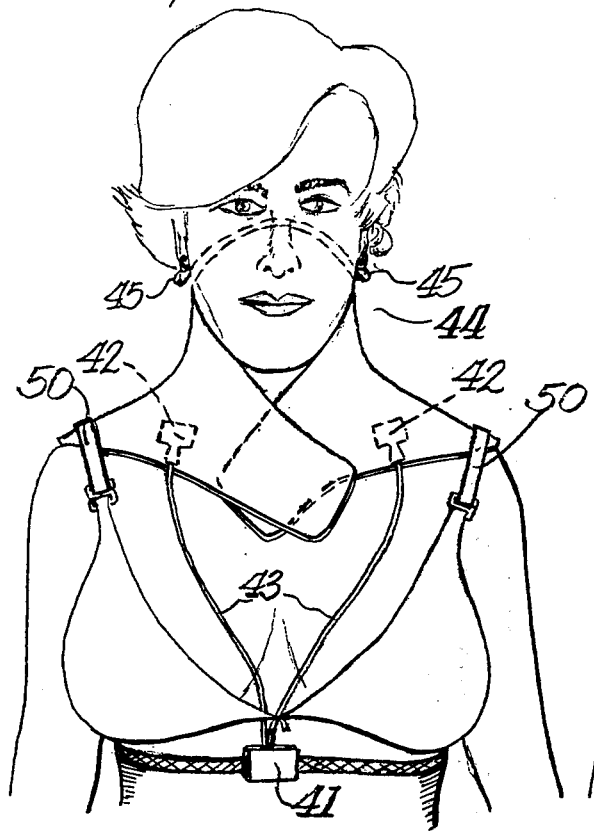
FIG. 10 is a front elevation view showing a modified collar in accordance with this invention.

FIGS. 1-2 illustrate a cervical collar 10 in accordance with this invention. As indicated therein the collar 10 includes a central section 12 which for the sake of convenience may be made from a pair of panels 14, 16 which are mirror images of each other. Central section 12 is so shaped and porportioned that its upper edge 18 is disposed at the occiput of the user while the lower edge 20 is at the dorsal-four of the user. Each panel 14, 16 terminates at the shoulder of the user and more specifically at the acromia. A further panel 22, 24 is attached to a respective panel 16, 14 for extending around the front of the user and panels 22, 24 terminate in flap sections 26 which overlap for securement to each other. Any suitable means of securement such as Velcro formations 28, may be utilized to secure the flaps 26 together. As is apparent from FIGS. 1-2 collar 10 thus includes a central occipitosinous section 12 with acromial wing sections 30 extending therefrom and flap sections 26 secured to each wing section 30. It is to be understood that the utilization of four individual panels 14, 16, 22, 24 is for illustrative purposes only and collar 10 may be made of a one piece construction or may include any number of panels. What is important is that the resultant structure includes the central occipito-sinous section 12 and the pair of acromial wing sections 30 and the flaps 26. Further, the lower peripheral edge of the body member 10 has a width which extends bicromially through the dorsal-four.

The specific shape of collar 10 has a number of distinct advantages. Foremost is the fact that by disposing the collar on the acromioclavicular joint pressure on the brachial plexus is minimized which not only facilitates the healing process but also adds greater comfort to the patient. Additionally, collar 10 is made from a suitable heat insulating material so that the body heat emitted over the generally large area covered by the collar is maintained and in effect recycled to the treated area.

Thus, collar 10 minimizes the pressure on the sensitive brachial plexus and spreads the pressure to the shoulder slope at the acromioclavicular joint while simultaneously maintaining the application of heat to the treated areas. This is of particular advantage over conventional collars which use a gravity concept resulting in pushing down on the muscles and nerves in the afflicted area.

Collar 10 is made of any suitable material which is heat insulating, soft and conformable to the anatomy of the user. Preferably such material is also stretchable and resilient. Suitable materials may include, for example, urea or other sponge materials, lycra, nylon or various absorbent materials. In use flaps 26 are pulled toward each other to overlap. The more the flaps are pulled, the greater the overlap and the tighter the collar becomes to thereby increase its support function.

In order to assure intimate contact of collar 10 with the user and thereby provide the necessary restriction of motion, stiffening means are incorporated in collar 10. In this respect in the illustrated embodiment the inner side or surface of each panel 14, 16 includes a pocket 32 which is open at its top 34 so that suitable stiffeners 36 (FIG. 7) may be removably inserted in the pockets 32. Stiffeners 36 may be made of any suitable material which is capable of being bent to assume a particular shape and then retain that shape. Such materials are well known and may, for example, be relatively thin gauge metal such as aluminum. In use the physician would bend the stiffeners to the desired shape for maximizing conforming the configuration of the collar 10 to the user's anatomy. If desired the stiffeners 36 may be permanently incorporated in the collar although it is preferred that the stiffeners be removable to readily permit replacement thereof and for cleaning or other purposes. Further, although two such stiffeners are illustrated it is to be understood that any suitable number and location may be incorporated in the collar within the concepts of this invention.

In accordance with a further feature of this invention the inner surface of collar 10 may be lined with an absorbent material 38 (FIG. 8) such as terry cloth for absorbing perspiration of the user. Liner 38 may be removable so that it can be readily cleaned or may be permanently attached to collar 10.

A further feature of this invention is that collar 10 may be made in different colors to complement the patient's apparel. This is particularly desirable when considering the relatively large visible area occupied by the collar. The choice of colors may be effected by forming the outer surface of the collar of any suitable color and providing sets of such collars for selection by the user. A more economical way of affording variety of color selection to the user, however, is the incorporation of an outer detachable layer 40 (FIG. 9) which may be detachably secured to collar 10 in any suitable manner. Thus a set of such outer layers 40 may be provided each of different colors or designs so that the user may change the outward appearance of collar 10 with each change in clothing.

In accordance with a further aspect of this invention the cervical collar is used as a means for mounting electrodes or sensors for direct contact with the skin of the user. In this respect it is frequently desirable to apply such devices to the user to sense conditions during treatment or, for example, to reduce pain by the application of electrical energy through electrodes. Conventionally, such devices as electrodes or sensors are mounted directly to the skin. The collar, however, affords a manner of mounting the electrodes which is not only more convenient to the physician but also more convenient to the patient. FIG. 10, for example, schematically illustrates electrodes 42 which are applied directly to the skin of the patient by being mounted to the inner surface of the collar. The electrodes may take any suitable shape or form. For example, electrodes 42 may be T & S electrodes which are mounted directly to the inside of the collar. The mounting may be accomplished by adhesive securement or epiductive tape. The electrodes may be formed as plates such as illustrated in FIG. 10 or as discs or as long strips or in any other suitable form. The utilization of a treating or support device such as a cervical collar which fits around the body as a means of mounting electrodes or sensors is a signficant aspect of this invention and its concepts may be employed not only in connection with cervical collars where, for example, electrodes might be mounted over the cervical dorsal nerves to reduce pain but may also be applied where electrodes or sensors are utilized on other parts of the body such as on the arms, chest, etc., where a treating device analogous to a cervical collar would be required apart from the requirement for such electrodes or sensors.

As illustrated in FIG. 10, electrodes 42 are connected to a battery or source of electrical energy 41 which may be disposed in any suitable location such as being strapped to the patient and battery 41 supplies power to the electrodes by transmission through conductive wires 43. Where such electrodes are used the material for the cervical collar is electrically non-conductive. Similarly, non-conductive stiffeners are used or conversely the stiffeners may be conductive if they are insulated.

FIG. 10 illustrates a modified form of the cervical collar which is particularly designed to maximize jaw movement thus permitting the patient to speak, swallow, etc. This is accomplished by providing an undercut or sloping sections in the upper edge 44 of the collar whereby the collar exposes the ear lobe and takes purchase just beneath the jaw thus barely grazing the jaw. In this manner there is minimal interference with jaw movement. Moreover, the patient may be permitted to wear earrings 45 without interference from the collar.

The cervical collar as previously described is particularly adaptable for both male and female patients. In accordance with further ramifications of this invention, however, the collar includes features particularly designed to overcome problems attendant with female patients and more particularly with such patients as are heavy breasted. In this respect with such patients undesirable pressure is applied to the sensitive brachial plexus from the weight of the breasts themselves or by having the bra pull down on the shoulders thus causing an adverse reaction. Collar 10, however, is designed to overcome these problems by distributing the weight of the breasts more effectively to minimize such pressure. In accordance with this invention means are provided to direct the application of weight of the breasts to the acromial areas. As illustrated in FIG. 1, for example, the acromial sections 30 include clips or hooks 46 in the general area of the acromioclavicular joint. The straps 48 of a generally conventional bra would be attached to hooks 46. The portion of the conventional bra straps attached to the back of the bra could be permitted to hang loosely or be tucked in the bra or would otherwise not be particularly secured. Conversely, hooks such as 46 may be provided both at the front and rear of the collar and bra straps would thereby be secured at both the front and rear.

FIG. 10 illustrates an alternative embodiment of this invention wherein the straps 50 of a conventional bra are simply disposed over the collar but are located more in the vicinity of the arcomioclavicular joint rather than being disposed closer to the neck as is conventionally worn. Because of the softness of the material used for the collar the straps 50 sink into the collar and thus are maintained in that location.

Figure 11:
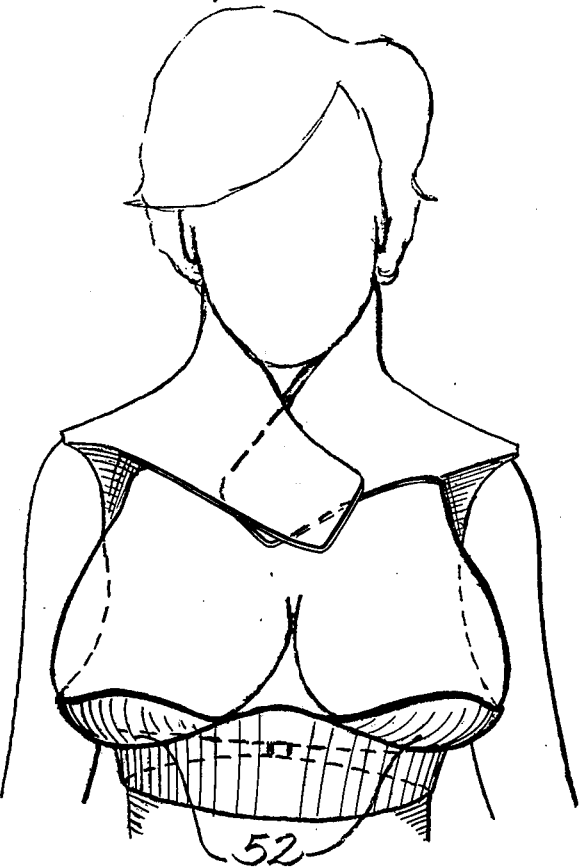
FIG. 11 is a front elevation view of still another modification of this invention shown in use.

FIG. 11 illustrates yet another form of this invention wherein a bra as such is completely omitted and replaced by support sections 52 which are connected to and form part of the collar and which are arranged to fit beneath the breasts for providing the necessary support. The details of sections 52 and their manner of extension from the collar may vary within the concept of providing such breast support as part of the collar itself. Thus sections 52 may be detachably secured to the collar for providing greater flexibility to accommodate different dimensional requirements for various patients or sections 52 may be permanently or integrally connected with the collar.

The cervical collar of this invention is particularly advantageous in that it is compatible with other treatments that might be simultaneously required for the patient. Thus, for example, a heart patient may wear a pacemaker without interference from the cervical collar. Similarly, the collar 10 would not apply undue pressure on and impair the cartid artieries so as not to cause vagal reflex. The aforenoted merely exemplify the numerous other treatments or conditions which are compatible with the cervical collar of this invention.

What is claimed is:

1. A cervical collar for applying body heat to the area of treatment and for minimizing pressure on the brachial plexus comprising a body member made from a material which is heat insulating and flexible and conformable to the anatomy of the user and capable of maintaining the body heat from the user to thereby apply heat to the treated area, said body member having a central occipito-sinous section for extending from the user's occiput to the dorsal-four of the user, an acromial wing section attached to each side of the central section and extending therefrom, each acromial wing section being disposed for resting on the acromioclavicular joint, said body member having a lower peripheral width which extends from one acromia to the other through the dorsal four (D-4), and a lower peripheral width extending from the occiput to each acromia, a flap section connected to each acromial wing section, and connecting means on said flap sections for securing said flap sections together when said body member is disposed on the user.

2. The collar of claim 1 wherein said material is stretchable and resilient whereby said flap sections may be pulled toward each other to overlap and simultaneously tighten said collar on the user, and said connecting means securing said flap sections together in an overlapped condition.

3. The collar of claim 2 including exposed pockets in said central section, and bendable stiffeners removably disposed in said pockets for closely conforming said collar to the anatomy of the user.

4. The collar of claim 3 including electrode means attached to the inner surface of said body member for being disposed against and in contact with the user's skin, electrical power means connected to said electrode means, and said body member being made of an electrically non-conductive material.

5. The collar of claim 4 including an absorbent inner liner attached to said inner surface of said body member for absorbing perspiration from the user, and said electrodes being attached to said body member by attachment to said liner whereby said liner is disposed between said electrodes and said body member.

6. The collar of claim 5 including a detachable outer layer detachably attached to the outer surface of said body member for complementing the apparel of the user.

7. The collar of claim 6 in combination therewith, a bra, and said bra having straps secured to said acromial sections of said body member for distributing the weight of the user's breasts away from the brachial plexus.

8. The collar of claim 7 including attaching means on said acromial sections, and said bra straps being secured to said attaching means.

9. The collar of claim 7 wherein said bra straps are disposed over said acromial sections and sink therein for securement to said body member.

10. The collar of claim 7 wherein the upper edge of each acromial section is sloped for exposing the user's ear lobes to permit the user to wear earrings and for making at most grazing contact with the user's jaw to permit jaw movement of the user.

11. The collar of claim 6 including breast support sections connected to said body member for supporting the user's breasts from underneath to thereby obviate the need for a bra.

12. The collar of claim 1 including electrode means attached to the inner surface of said body member for being disposed against and in contact with the user's skin, electrical power means connected to said electrode means, and said body member being made of an electrically non-conductive material.

13. The collar of claim 1 including an absorbent inner liner attached to the inner surface of said body member for absorbing perspiration from the user.

14. The collar of claim 1 including an outer layer detachably connected to the outer surface of said body member for complementing the apparel of the user.

15. The collar of claim 1 including stiffeners secured to said body member for conforming to the anatomy of the user.

16. The collar of claim 15 including exposed pockets on the inner surface of said central section, and said stiffeners being removably disposed in said pockets.

17. The collar of claim 1, in combination therewith, a bra, and said bra having straps secured to said acromial sections of said body member for distributing the weight of the user's breasts away from the brachial plexus.

18. The collar of claim 1 wherein the upper edge of each acromial section is sloped for exposing the user's ear lobes to permit the user to wear earrings and for making at most grazing contact with the user's jaw to permit jaw movement of the user.

19. The collar of claim 1 including breast support sections connected to said body member for supporting the user's breasts from underneath to thereby obviate the need for a bra.

20. A method of treating the cervical area of a human patient comprising applying a cervical collar having free ends thereof to the patient, disposing the collar against the patient over a length from the occiput to the dorsal-four and over a width from one acromia to the other through the dorsal-four to distribute pressure away from the brachial plexus and to the acromioclavicular joints, pulling the free ends toward each other with the free ends overlapping, securing the overlapped free ends together, the patient being a woman wearing a bra, and including the step of securing the straps of the bra to the collar.

21. The method of claim 20 including securing electrodes to the inner surface of the collar, disposing the thus secured electrodes in contact with the patient's skin, and applying electrical energy to the electrodes.

22. The method of claim 20 including securing the straps in the general area of the acromioclavicular joints.

* * * * *